United States Patent [19]

Rogers

[11] 4,345,105
[45] Aug. 17, 1982

[54] REDUCING METHYLACETYLENE CHARGED TO AN ETHYLENE PRODUCTION

[75] Inventor: David L. Rogers, Demopolis, Ala.

[73] Assignee: Phillips Petroleum Company, Bartlesville, Okla.

[21] Appl. No.: 177,314

[22] Filed: Aug. 12, 1980

[51] Int. Cl.$^3$ .......................... C07C 5/05; C07C 4/02; C07C 2/00; C07C 5/00
[52] U.S. Cl. .................................... 585/271; 585/500; 585/648
[58] Field of Search ........................ 585/271, 500, 648

[56] References Cited

U.S. PATENT DOCUMENTS 3,505,304   4/1970   Davison et al. ................ 585/271 X
3,673,270   6/1972   Gosser .................................. 585/271

Primary Examiner—Paul F. Shaver

[57] ABSTRACT

Methylacetylene is removed prior to unduly raising its temperature from a stream containing the same but thus to minimize any danger of violent decomposition or explosion or coke formation. In one embodiment, a stream is obtained from the cracking of propane to produce ethylene, is fractionated to obtain a concentrate of methylacetylene and any propadiene which may be present, the concentrate is subjected to hydrogenation, thus converting methylacetylene and propadiene to propylene and the propylene is recovered. A fractionation tower or system operation is shown wherein a propane-propylene concentrate from an ethylene fractionation unit is fed to a fractionator from which non-condensibles and propylene are taken off as overhead, and upper sidedraw, respectively, an intermediate fraction containing methylacetylene and propadiene which may be present is taken from the system for hydrogenation, the hydrogenated stream being returned to the fractionator, and a bottoms yield, which is reboiled, is drawn off and can be sent for further cracking, as to produce ethylene.

6 Claims, 1 Drawing Figure

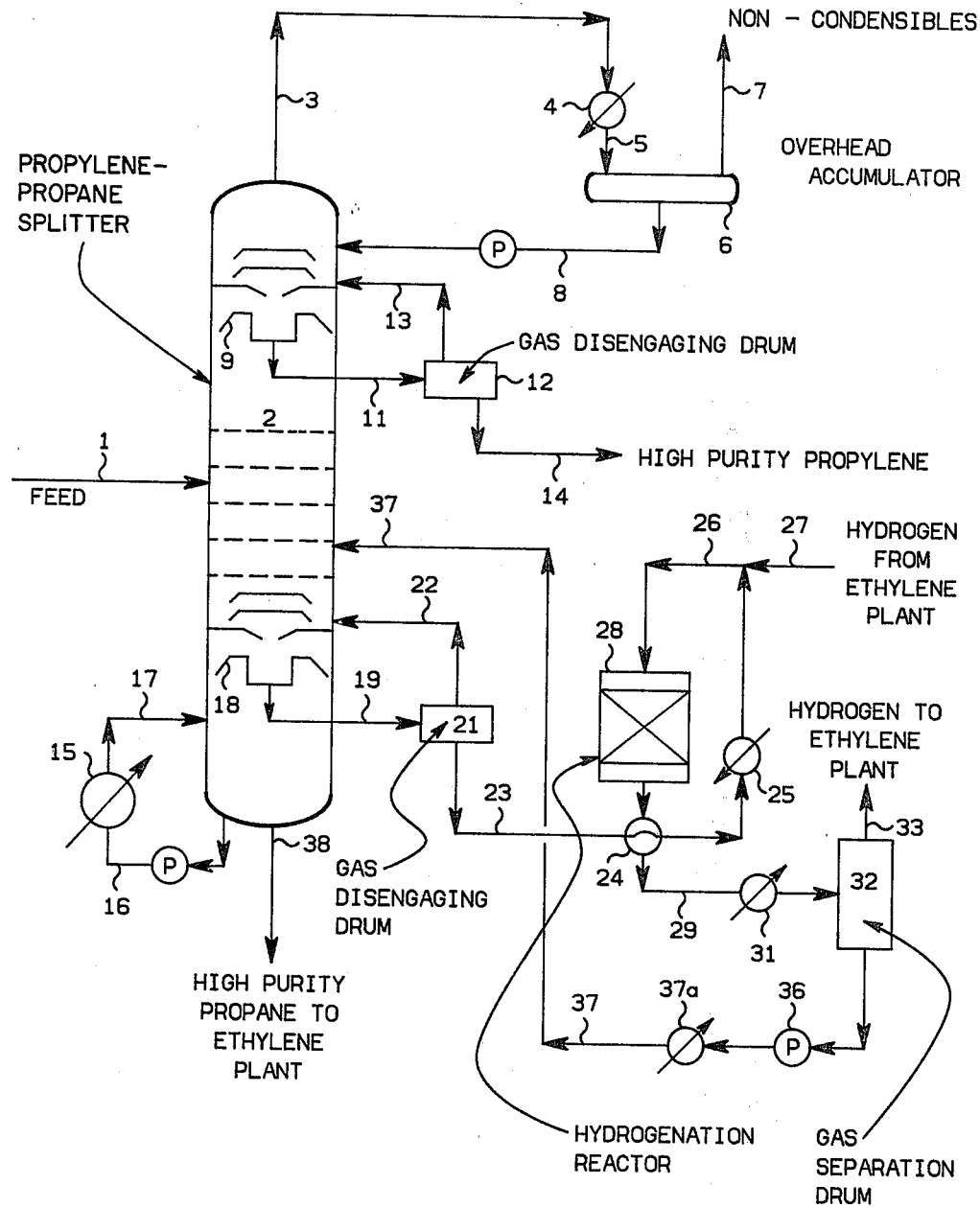

REDUCING METHYLACETYLENE CHARGED TO AN ETHYLENE PRODUCTION

BRIEF DESCRIPTION OF THE INVENTION

Methylacetylene in a stream resulting from the cracking of propane-containing stream to produce ethylene, and containing propylene, propane, methylacetylene, and propadiene, is fractionated to produce a stream containing propane, propylene, methylacetylene and propadiene. Methylacetylene-propadiene concentrate is charged to a hydrogenation following which, after a gas separation step, the mass is returned to the fractionation to recover produced propylene.

DETAILED DESCRIPTION

This invention relates to the production of ethylene. It also relates to making more safe the production of ethylene. Still further, it relates to the removal of methylacetylene from a cracked stream obtained upon the conversion of propane to produce ethylene. In one of its aspects, the invention relates to the obtaining of a stream containing methylacetylene in which the methylacetylene can be hydrogenated with good results. In one of its concepts, the invention provides a method for the removal of methylacetylene from a cracked stream resulting upon cracking propane to produce ethylene which comprises fractionating the cracked stream to remove therefrom a stream rich in methylacetylene and relatively poor in propylene and subjecting such stream to hydrogenation to convert methylacetylene therein to propylene. In another of its concepts, the invention provides a combination operation in which propane is cracked to produce an ethylene containing stream also containing propylene, propane, methylacetylene and propadiene and some non-condensibles, fractionating said stream to produce at least a high purity propylene product or fraction, a stream rich in propane in which there has been concentrated methylacetylene, and a propane enriched bottoms stream, hydrogenating the stream rich in methylacetylene to produce propylene therefrom, and returning the hydrogenated stream to the fractionation. In a still further concept of the invention, now preferred, there is built up by recycle through the fractionation and from the hydrogenation, a cycling stream which will be at least, on a weight basis, one-half times to about 2 or more times, larger than the feed to the fractionation, thus to create a cycling pool rich in propane with which to charge the methylacetylene for its hydrogenation therein. Apparently, the recycle of the propane-rich hydrogenation effluent is beneficial in the concentration of methylacetylene at this locus in the tower.

Methylacetylene is an explosive compound. It should not be permitted to become unduly concentrated. In the fractionation of a cracked propane stream containing methylacetylene for removal therefrom of ethylene, propylene and other components, there results unconverted propane which is easily recycled to the cracking operation. The potentially explosive methylacetylene should not be allowed to build up and to be returned to the propane cracking or ethylene production system.

In U.S. Pat. No. 3,679,763, issued July 20, 1972, disclosing purification of process step streams by hydrogenation, for example, gases derived from the pyrolysis of, for example, butane, kerosene, naphtha, refinery gases, and other mineral oil and gas oil fractions, there is disclosed the removal of acetylene from the cracked gases before these are useable as raw materials for plastics. Upon disclosure, this partially sulfided catalyst supports a high degree of selectivity in hydrogenating acetylenes to the olefins, and that there is no selectivity between acetylene and diene, dienes being the desired product. The patent further discloses that a $C_4$ stream is generally removed prior to the selected hydrogenation reaction. It is disclosed that butylene, butadiene, propylene, and ethylene are removed from a gas stream also containing acetylene, methylacetylene, and propadiene by hydrogenating the acetylene with minimal hydrogenation of butylene, butadiene, propylene and ethylene. There is shown in the patent in the operation therein described in connection with the drawing a depropanizer from which a $C_3$ effluent stream is selectively hydro-treated to hydrogenate methylacetylene and propadiene to propylene. The disclosure of the patent is included herein by reference.

It is an object of this invention to remove from a stream obtained by the cracking of propane to produce ethylene the small amount of methylacetylene also produced. It is another object of this invention to improve the economics and safety involved in the removal of methylacetylene from a cracked propane stream containing same. It is a further object of the invention to convert methylacetylene in a stream containing the same to produce propylene from the stream. It is a still further object of the invention to hydrogenate methylacetylene.

Other aspects, concepts, objects and the several advantages of the invention are apparent from a study of this disclosure, the drawing and the appended claims.

According to the present invention, a stream containing methylacetylene, e.g., as obtained from a cracking of propane to produce ethylene and propylene, is treated to produce therefrom a stream containing a major proportion of propylene, a minor proportion of propane and a relatively very small amount of methylacetylene; the thus obtained propane-propylene-methylacetylene concentrate, which may contain a small amount of propadiene, is fractionated to produce: a high purity propylene product, a fraction containing propane, a minor amount of propylene, methylacetylene and any propadiene present in the original stream, passing said fraction to hydrogenation and hydrogenating methylacetylene and any propadiene to propylene, returning said now hydrogenated fraction of a locus near that from which it has been obtained; and a bottom fraction enriched in propane and containing only a few parts per million methylacetylene. In a now preferred embodiment of the invention, a stream and fraction described are obtained in a unitary fractionation tower or system, the bottoms of which are heated for suitable operation of the tower or system. Thus, the bottoms are reboiled in a reboiler.

According to the invention, decomposition or even explosion of methylacetylene in the tower bottoms in the bottom of the tower and especially in the reboiler where high reboiler heat transfer surface temperatures are encountered, are minimized and, indeed, altogether avoided as when the bottoms will contain only a few parts per million, e.g., five parts per million, methylacetylene by weight.

DESCRIPTION OF DRAWINGS

The drawing shows a now preferred flow diagram wherein a fractionation is effected in a so-called propylene-propane splitter tower 2. A propane-propylene concentrate as can be obtained from the propane cracking unit for the production of ethylene enters at 1. A separation between propane and propylene takes place. Overhead vapor 3 taken off at about 106° F. and at a pressure of about 245 psia is cooled and partially condensed at 4 and passed by 5 into overhead accumulator 6 from which non-condensibles are taken off at 7. A liquid reflux returns to the tower by way of 8. From trap-out tray 9, a high purity propylene product is removed by 11, degassed at 12 and a high purity product removed at 14. Gases and any vapors are passed by 13 into the column above tray 9.

According to the invention, from trap-out tray 18 there is removed at 19 a liquid stream rich in methylacetylene. This stream is passed to a gas disengaging drum 21, vapor being returned to tower 2 at 22, and liquid stream, comprising propane and containing some propylene and, importantly, a high concentration of methylacetylene, is removed at 23. Such a stream, as shown in the tabulation given below, may contain about 52 percent propane, 30 percent propylene, 13 percent methylacetylene, and about 5 percent propadiene, all on a weight basis. This stream 23 is cooled in heat exchanger 24, further cooled at 25 and passed by 26 together with hydrogen introduced at 27 to hydrogenation reactor 28, wherein the methylacetylene and any propadiene are hydrogenated to produce propylene. Bottoms 29 from hydrogenation 28 are passed to cooling at 31 and to gas separation drum 32. Hydrogen is taken off at 33 and liquid is pumped by pump 36 by way of 37, heated at heater 37a to tower 2, and as shown in this embodiment, introduced into tower 2 above take-off tray 18. The conditions in the bottom of the tower are maintained by flow of liquid 16 to reboiler 15 and returning heated fluid to the tower 2 by 17, and include a temperature of 130° F. and 268 psia.

Bottoms 38 constitute a propane recycle for the production of ethylene or other purpose as may be desired.

It can be seen that substantially complete conversion of methylacetylene and any propadiene occurs in the system of the invention so that the propane passing through the reboiler or for recycle presents no "explosive" danger in the splitter reboiler while considerably minimizing coke formation in the reboiler and, of course, in the cracking furnace to which it may be recycled for further cracking. Calculated example follows.

| 1 Feed Stream | |
|---|---|
| Pounds/hour | 19,620 |
| Composition, Wt. % | |
| Propylene | 87.30 |
| Propane | 12.04 |
| Methylacetylene | 0.48 |
| Propadiene | 0.18 |
| Total | 100.00 |
| 7 Non-Condensibles | |
| Pounds/hour | 70 |
| 8 Reflux, pounds/hour | 259,000 |
| 14 High Purity Propylene | |
| Pounds/hour | 17,300[a] |
| Composition, Wt. % | |
| Propylene | 99.5 |
| Propane | 0.5 |

[a]Gain of 157 pounds per hour of 99.5 weight percent purity propylene by the invention, as compared with conventional operation without hydrogenation.

| 23 Lower Side Draw Liquid | |
|---|---|
| Pounds/Hour | 24,500 |
| Composition, wt. % | |
| Propane-Propylene (52%, 30%) | 82 |
| Methylacetylene | 13 |
| Propadiene | 5 |
| 27 Hydrogen | |
| Pounds/hour | 3,450 |
| 33 Gas Removed | |
| Pounds/hour | 3,440 |
| 37 Liquid/Return | |
| Pounds/hour | 24,510 |
| 38 Propane Recovery | |
| Pounds/hour | 2,250 |
| Composition, Wt. % | |
| Propane | 99.0 |
| Propylene | 1.0 |
| Methylacetylene (ppm by wt.)[b] | (5) |
| Propadiene (ppm by wt.)[b] | (10) |

[b]Reported as parts per million by weight. Substantially complete conversion of methylacetylene and propadiene occurs in system of invention so that the recycle propane has no "explosive" danger in the splitter reboiler and coke formation therein and in the furnaces from the methylacetylene and propadiene is reduced.

| Operating Conditions | |
|---|---|
| 2 Splitter | |
| Top Pressure, psia | 245 |
| Top Temperature, °F. | 106 |
| Bottom Pressure, psia | 268 |
| Bottom Temperature, °F. | 130 |
| 6 Overhead Accumulator | |
| Pressure, psia | 240 |
| Temperature, °F. | 90 |
| 23 Lower Side Draw Liquid | |
| Temperature, °F. | 111 |
| 26 Feed to Unit 28 | |
| Temperature, °F. | 75 |
| 37 Liquid Return | |
| Temperature, °F. | 105 |
| 28 Hydrogenation Zone | |
| Pressure, psia | 260 |
| Temperature, °F. | 80 |
| Catalyst: Palladium on alumina (conventional) | |
| Space Velocity, Liquid Volume/Volume Catalyst/Hour | 2 |

One skilled in the art in possession of this disclosure having studied the same will understand that depending upon the size and conditions in the hydrogenation reactor the stream taken by 19 from tray 18 can be built up as may be desired. Such consideration as the hydrogenation, evolution of heat, etc., will be taken into account. The invention provides a flexibility of operation permitting the operator to trap out and to convert methylacetylene to propylene, which methylacetylene otherwise may cause serious problems.

Without the use of hydrogenation zone 28 of the invention, stream 38 contains about 91.5% propane, 3.0% propylene, 4.0% methylacetylene, and 1.5% propadiene, all by weight. With the use of hydrogenation zone 28 of the invention, stream 38 contains about 99.0% propane, and about 1.0% propylene, along with only about 5 parts per million methylacetylene and only about 10 parts per million propadiene, all by weight. Thus, the invention greatly reduces or substantially eliminates methylacetylene and propadiene in the propane-rich stream so as to minimize danger of violent explosions from methylacetylene when heating said propane rich stream, and also the production of additional propylene from this recovered methylacetylene and propadiene.

Reasonable variation and modification are possible within the scope of the foregoing disclosure, the drawing and the appended claims to the invention, the essence of which is that there has been provided a process for the removal of methylacetylene and any propadiene from a stream containing the same together with substantial amounts of propane and propylene, and can be obtained from a propylene cracking unit for the production of ethylene, the process comprising fractionating a feed to obtain therefrom a fraction containing a concentrate of methylacetylene, hydrogenating the methylacetylene in such fraction to produce propylene from methylacetylene and from any propadiene present and recycling said fraction, as described.

I claim:

1. A process for the elimination of methylacetylene which comprises:
   (a) in a fractionation zone, fractionating a stream containing propane, propylene and methylacetylene to obtain a fraction of enriched methylacetylene content;
   (b) passing said fraction to a hydrogenation zone; and
   (c) hydrogenating the methylacetylene in said fraction.

2. A process in accordance with claim 1 wherein said stream and said fraction also contain propadiene; and wherein said propadiene is also hydrogenated in said hydrogenation zone.

3. A process in accordance with claim 1 wherein said fraction, after hydrogenation, is further processed to obtain a high purity propylene fraction and a high purity propane fraction.

4. A process in accordance with claim 3 wherein said fraction, after hydrogenation, is recycled to said fractionation zone.

5. A process in accordance with claim 1 wherein said stream contains predominantly a propane-propylene concentrate as can be obtained from a propane cracking unit for the production of ethylene.

6. A process in accordance with claim 1 wherein said stream is fractionated to produce
   (a) a propylene enriched overhead fraction,
   (b) a fraction of enriched methylacetylene content containing also propane and propylene and
   (c) a propane enriched bottoms fraction.

* * * * *